United States Patent [19]

Matkovich

[11] Patent Number: 4,798,676
[45] Date of Patent: Jan. 17, 1989

[54] LOW PRESSURE DROP BACTERIAL FILTER AND METHOD

[75] Inventor: Vlado I. Matkovich, Glen Cove, N.Y.

[73] Assignee: Pall Corporation, East Hills, N.Y.

[21] Appl. No.: 196,896

[22] Filed: May 18, 1988

Related U.S. Application Data

[63] Continuation of Ser. No. 943,492, Dec. 19, 1986, abandoned.

[51] Int. Cl.⁴ ............................................. B01D 35/02
[52] U.S. Cl. ..................................... 210/767; 210/445; 210/446; 55/498; 55/500; 55/521; 128/206.16
[58] Field of Search ................ 210/767, 445, 446; 55/498, 500, 521; 128/200.24, 205.27, 206.16, 206.17, 206.19, 206.22

[56] References Cited

U.S. PATENT DOCUMENTS

| | | | |
|---|---|---|---|
| 2,859,747 | 11/1958 | Stampe | 128/206.16 |
| 3,494,466 | 2/1970 | Rose et al. | 210/446 |
| 3,765,536 | 10/1973 | Rosenberg | 210/446 |
| 3,765,537 | 10/1973 | Rosenberg | 210/446 |
| 3,803,817 | 6/1974 | Lewis | 55/498 |
| 3,815,754 | 6/1974 | Rosenberg | 210/445 |
| 3,880,627 | 4/1975 | Morton | 210/446 |
| 3,979,295 | 9/1976 | Markley | 210/445 |
| 4,187,182 | 2/1980 | Rosenberg | 210/446 |
| 4,360,018 | 11/1982 | Choksi | 55/498 |
| 4,386,948 | 6/1983 | Choksi et al. | 55/499 |

*Primary Examiner*—Richard V. Fisher
*Assistant Examiner*—Wanda L. Millard
*Attorney, Agent, or Firm*—Leydig, Voit & Mayer

[57] ABSTRACT

Filter and method for filtering bacteria-laden saliva droplets and aerosols from human breath particularly suitable for use in pulmonary function testing where a low pressure drop is required. A relative large pore filter medium is oriented at a large angle relative to the overall flow through the filter such that both larger droplets and smaller aerosols impact and are retained on the filter medium.

4 Claims, 1 Drawing Sheet

LOW PRESSURE DROP BACTERIAL FILTER AND METHOD

This application is a continuation of application Ser. No. 943,492 filed 12-19-86, now abandoned.

TECHNICAL FIELD OF THE INVENTION

This invention relates to a bacterial filter and method particularly suitable for use with pulmonary function testing apparatus for testing of one's breathing faculties.

BACKGROUND

It is desirable to filter the patient's exhaled air to keep the intricate and difficult-to-clean bellows isolated from an individual's saliva and bacteria.

Bacterial filtration in pulmonary function testing presents multiple conditions which are difficult to satisfy simultaneously. For convenience and economic reasons, it is desirable that the filter be inexpensive enough to be disposable after use with a patient. It is also desirable that the volume of the filter be sufficiently small that it does not significantly affect the flow dynamics of the exhaled air within the testing device. Finally, it is important that any filtration device not introduce a flow restriction which might affect the results of the testing.

Small, disposable filters with filter media suitable for filtering bacteria from air are known. One example of such a commercial filter is a BB-50 filter manufactured by the present assignee and employing a fiberglass filter medium. The basic filter construction is similar to that disclosed in U.S. Pat. No. 3,815,754. Such a filter generates a sufficiently large pressure drop, however, that it is unsuitable for use in pulmonary function testing where it is important not to introduce significant flow restrictions. More open filter media, which might solve the pressure drop problem in a small and inexpensive filter, may not provide sufficient filtration, especially of the small aerosolized saliva droplets associated with high velocities encountered in deep, forceful breathing. A need exists for a small, inexpensive filter which provides sufficient filtration with an acceptably low pressure drop. A pressure drop of about 0.3 inches of water at a flow of about 500 liters per minute is considered to be acceptably low.

It is, accordingly, the primary object of the present invention to provide an inexpensive filter suitable for use in filtering human breath which has both a high bacterial retention efficiency and a low pressure drop.

It is a further object of the present invention to provide an effective, yet small and disposable filter unit suitable for use in pulmonary function testing.

These and other objects will be apparent from the following detailed description and associated drawings.

DETAILED DESCRIPTION OF THE PREFERRED EMBODIMENT

The instant invention provides a solution to the difficult problem of inexpensively providing a high bacterial filtration efficiency while generating an extremely low pressure drop. This is accomplished by using a relatively open filter medium oriented in a manner which assures a high degree of both droplet and aerosol removal.

In order to fully appreciate the principle of operation of the present invention it is helpful to understand the mechanisms for bacterial expulsion from the mouth through breathing. As an initial point, it has been recognized that bacteria are expelled from the mouth with saliva in either small aerosol or larger droplet form. As used herein, the distinction between an "aerosol" and a "droplet" is a subjective one, the former term contemplating a substantially suspended particle and the latter term contemplating a particle large enough to be influenced by gravity.

Whether aerosols or droplets are formed depends upon the velocity of the air being exhaled past the moist inner surfaces of the throat and mouth. Significantly, at normal breathing velocities, no droplets or aerosols are formed. As a result, air exhaled at normal breathing velocities has a low bacterial content. It is only at higher-than-normal velocities that saliva droplets are formed and at even higher velocities that saliva aerosols are formed. It is under these higher velocity conditions that exhaled breath has a significant bacterial level. The present invention recognizes this phenomenon in selecting the type of filter medium and its orientation across the air stream.

The instant invention employs a low pressure drop filter medium with pores small enough to stop the largest droplets contemplated, but deliberately larger than the smallest aerosol contemplated. As a result of the orientation of the filter medium, however, the filter is nevertheless effective in stopping a very high percentage of even those aerosols which are smaller than the filter pore sizes. According to the invention, the filter medium is oriented at a relatively high angle relative to the overall air flow, preferably in the range of about 160° to 175°, such that the effective pore size normal to the incoming flow direction is about the size of the aerosol. With such an arrangement, the inertia of the aerosol will cause it to impact some point of the periphery of the pore despite the fact that the pore, viewed normal to the plane of the filter medium, is larger than the aerosol. Whereas the aerosol, if approaching the filter media normal to it's surface, might pass through a larger pore without impacting the filter medium, it will not pass through the angled filter medium. Hence, it is contemplated that filter media with pores in the range of about 50 microns to about 200 microns are suitable for filtering both droplets and aerosols with a minimal pressure drop.

Figure 1:
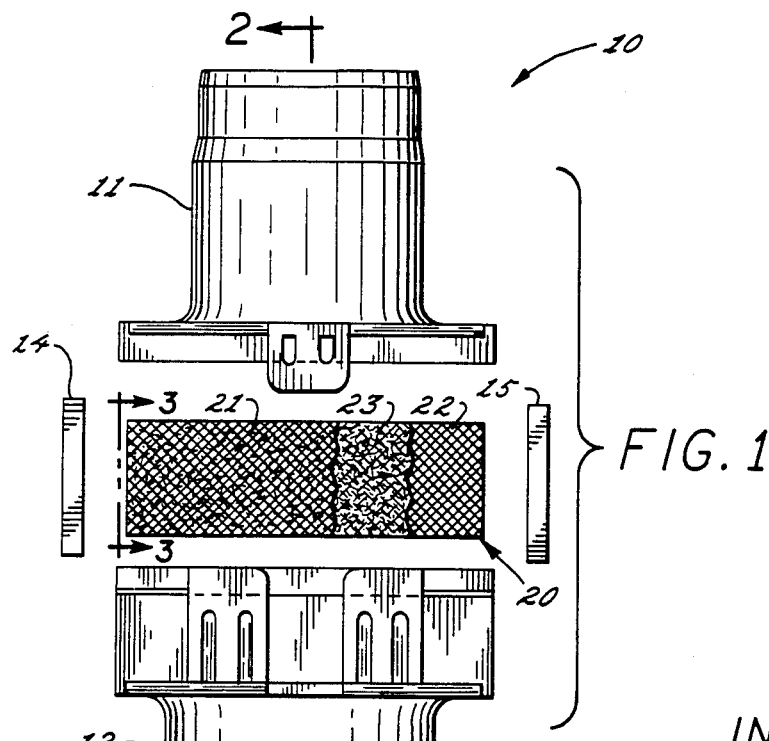
FIG. 1 is an exploded view of a filter assembly according to the present invention and suitable for pulmonary function testing.

The figures illustrate a preferred embodiment of the present invention. FIG. 1 is a perspective view of a disposable filter specifically adapted for use with apparatus for pulmonary function testing. When used with such apparatus it is contemplated that the filter be placed at or near the mouth, i.e., within a few inches thereof. This location in close proximity to the mouth serves, eliminates or at least reduces the amount of the apparatus upstream of the filter which must be disposed of or cleaned between use of the apparatus by successive patients. As a related point, the location near the patient's mouth also permits the filter to intercept the air at a point where the velocity and nature of the aerosols or droplets are substantially the same as when exiting the mouth. One specific embodiment of the filter shown has inlet and outlet diameters of about 27 and 31 millimeters respectively, with a total internal volume of only about 70 cubic centimeters (including both connectors), with the result that the flow conditions of the air leaving the mouth are substantially maintained through the filter and into the pulmonary function testing apparatus.

The filter illustrated in the figures is of the same basic construction as the disposable box filter disclosed in U.S. Pat. No. 3,815,754 to Rosenberg and assigned to the present assignee. As best shown in the exploded view of FIG. 1, the filter comprises five components, an upper filter housing and inlet 11, a lower filter housing and outlet 12, end caps 14 and 15, and laminated filter medium 20. The details of the construction are disclosed in the referenced patent, the disclosure thereof being incorporated herein by reference.

According to an aspect of the invention the diameters of the inlet and outlet (noted above for the one specific embodiment) are large relative to the size of the main filter housing (approximately $38 \times 47 \times 17$ millimeters, internal dimensions, for the same specific embodiment) to reduce pressure drop and to result in a generally axial flow of air (represented by the arrow in FIG. 2) through the filter.

Figure 3:
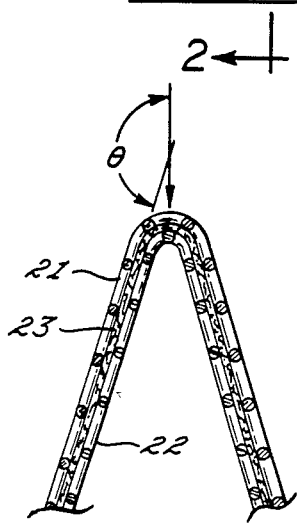
FIG. 3 is a partial cross-sectional detail of the filter medium employed in the filter assembly of FIGS. 1 and 2.
Figure 2:
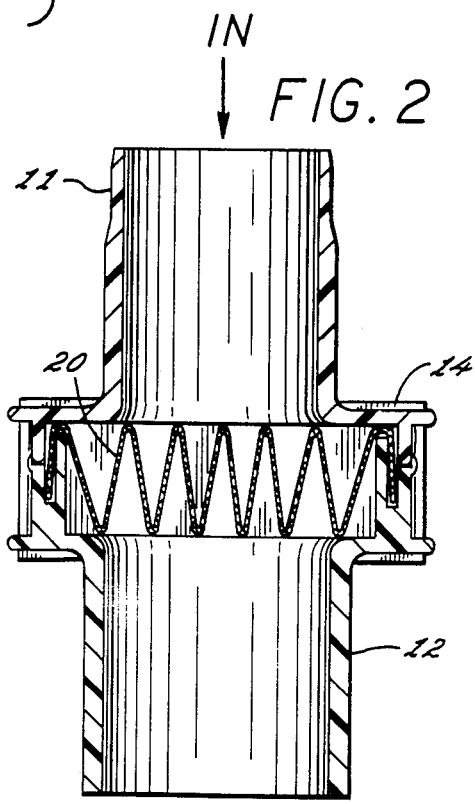
FIG. 2 is a cross-sectional view of the filter assembly of FIG. 1.

Referring to FIGS. 2 and 3, the filter medium 20 is sharply pleated to result in a series of surfaces oriented at a large angle $\theta$ relative to the direction of air flow. In the embodiment shown the angle between the air flow and the central pleats is approximately 165°. Sharp pleating is desirable to minimize the area of filter medium normal, or substantially normal, to the air flow.

The specific filter medium employed may vary. One particularly advantageous medium is a 3 layer laminate, illustrated in the detailed cross section of FIG. 3, consisting of outer support layers 21 and 22 of coarse (approximately 1 millimeter pore size) polypropylene mesh with an inner filtration layer 23 of non-woven hydrophobic polypropylene having a pore size of approximately 120 microns. Such a filter medium employed in the specific filter embodiment discussed above was found to generate a pressure drop of only about 0.3 inches of water at an air flow rate of about 500 liters/minute.

A low pressure bacterial filter of the type described above was tested for its efficiency in removing aerosols and droplets at flow rates approximating breathing conditions. One condition tested was a high-speed exhalation of a single human breath, estimated to be approximately 500 liters per minute, resulting in a small droplet, high flow rate challenge. This simulated the actual challenge for a filter used in a single breath pulmonary function machine. The control was the same challenge without filtration. The filter bacterial retention was found to be at least 99%.

The filter was also challenged with large bacteria-filled droplets produced by a disposable plastic nebulizer with the deflector removed. The humid make-up air was generated by a respirator with a maximum flow rate set to about 50 liters per minute. The bacteria in ten cycles (breaths) constituted the challenge. Again, the control was the challenge without filtration. The filter bacterial retention for this challenge was found to be greater than 99.9%.

Thus a small and inexpensive bacterial filter for breathing circuits has been described which exhibits very low pressure drops at relatively high flow rates while effecting a high degree of bacterial removal over a range of breathing conditions. It will be appreciated that the present invention is not limited to the embodiment shown and described but, on the contrary, extends to other embodiments and variations within the spirit and scope of the appended claims.

I claim:

1. A method of filtering bacteria from exhaled human breath in a pulmonary function apparatus comprising passing the exhaled human breath through a housing disposed in close proximity to the mouth, the housing having an inlet, an outlet, and a filter medium disposed therebetween, the inlet and the outlet being sized relative to the housing to result in flow of exhaled breath through the inlet, through the filter medium, and out of the outlet at substantially the same velocity as when exhaled from the mouth, the filter medium having a nominal pore size in the range of about 50 microns to about 200 microns, the surface of the filter medium being dipsoed at an angle of at least about 160° relative to the direction of the breath approaching the filter medium whereby substantially all saliva droplets and aerosols impact upon and are retained by the filter medium.

2. The method of filtering the claim 1 wherein the filter medium is a layer of nonwoven polypropylene having a nominal pore size of about 120 microns.

3. The method of filtering of claim 2 wherein the filter medium is supported by at least one layer of coarse polypropylene mesh.

4. The method of filtering of claim 3 wherein the filter medium is disposed between layers of polyproplene mesh having a nominal pore size of at least about 1 millimeter.

* * * * *

UNITED STATES PATENT AND TRADEMARK OFFICE
CERTIFICATE OF CORRECTION

PATENT NO. : 4,798,676
DATED : January 17, 1989
INVENTOR(S) : Vlado I. Matkovich It is certified that error appears in the above-identified patent and that said Letters Patent is hereby corrected as shown below:

In the Claims:

Claim 1, col. 4, line 38, delete "dipsoed" and substitute --disposed--;

Claim 2, col. 4, line 44, delete "the", first occurrence, and substitute --of--.

Signed and Sealed this

Seventeenth Day of October, 1989

Attest:

DONALD J. QUIGG

Attesting Officer

Commissioner of Patents and Trademarks